United States Patent [19]

Foucras

[11] 4,038,519
[45] July 26, 1977

[54] ELECTRICALLY HEATED FLEXIBLE TUBE HAVING TEMPERATURE MEASURING PROBE

[75] Inventor: Jacques Foucras, Bron, France

[73] Assignee: Rhone-Poulenc S.A., Paris, France

[21] Appl. No.: 524,210

[22] Filed: Nov. 15, 1974

[30] Foreign Application Priority Data

Nov. 15, 1973 France ............................. 73.40688
Oct. 7, 1974 France ............................. 74.33694

[51] Int. Cl.² ............... H05B 3/58; A61M 5/14; F16L 11/12; F24H 1/10
[52] U.S. Cl. ............................. 219/301; 128/214 A; 138/33; 138/133; 174/47; 219/505; 219/522; 338/23
[58] Field of Search ............... 219/301, 535, 504, 505, 219/522; 174/47; 128/214 A; 138/33, 133; 338/22 R, 23; 222/146 HE, 146 R; 137/341

[56] References Cited

U.S. PATENT DOCUMENTS

| | | | |
|---|---|---|---|
| 641,306 | 1/1900 | Lawton | 219/301 |
| 1,995,302 | 3/1935 | Goldstein | 219/301 UX |
| 2,274,839 | 3/1942 | Marick | 219/301 X |
| 2,516,864 | 8/1950 | Gilmore et al. | 219/301 UX |
| 2,530,105 | 11/1950 | Wallace | 174/47 UX |
| 2,745,074 | 5/1956 | Darling | 174/47 X |
| 2,793,280 | 5/1957 | Harvey | 219/301 UX |
| 3,189,053 | 6/1965 | Parr | 138/133 |
| 3,585,361 | 6/1971 | Rosen et al. | 219/301 UX |
| 3,603,403 | 9/1971 | Horwinski | 174/47 UX |
| 3,803,385 | 4/1974 | Sandorf | 219/301 UX |

*Primary Examiner*—A. Bartis
*Attorney, Agent, or Firm*—Stevens, Davis, Miller & Mosher

[57] ABSTRACT

A flexible heating tube especially for medical use, e.g. for taking blood away from and returning it to the body, in which a flexible pipe of transparent plastics material is provided with at least one electrical helical resistance heating conductor and at least one helical filiform temperature measuring resistance probe. The two elements are wound on the same axis and are embedded in the wall of the pipe and are in surrounding relation to the bore in the pipe. The helical turns of the at least one electrical resistance conductor and of the at least one temperature measuring probe are of the same pitch and are coextensive along the length of the pipe. Electrical connection terminals at at least one end of said pipe are connected to said at least one heating conductor and said at least one temperature measuring probe.

12 Claims, 8 Drawing Figures

U.S. Patent  July 26, 1977  Sheet 1 of 3  4,038,519
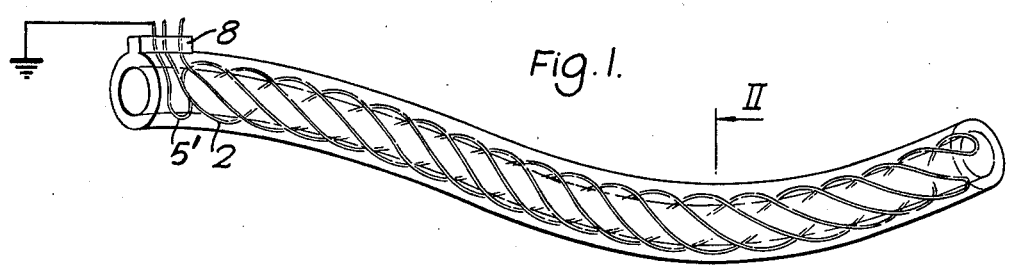
Fig. 1.
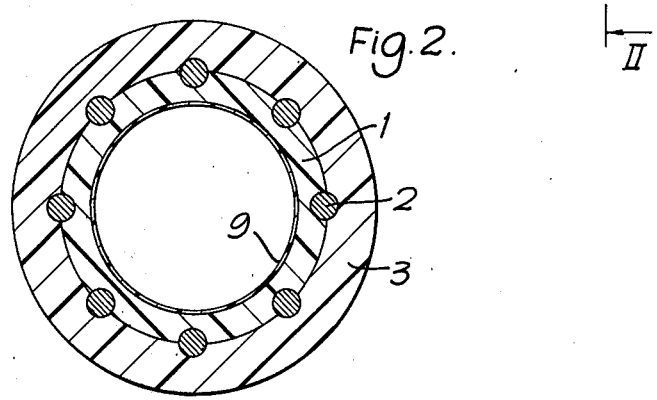
Fig. 2.
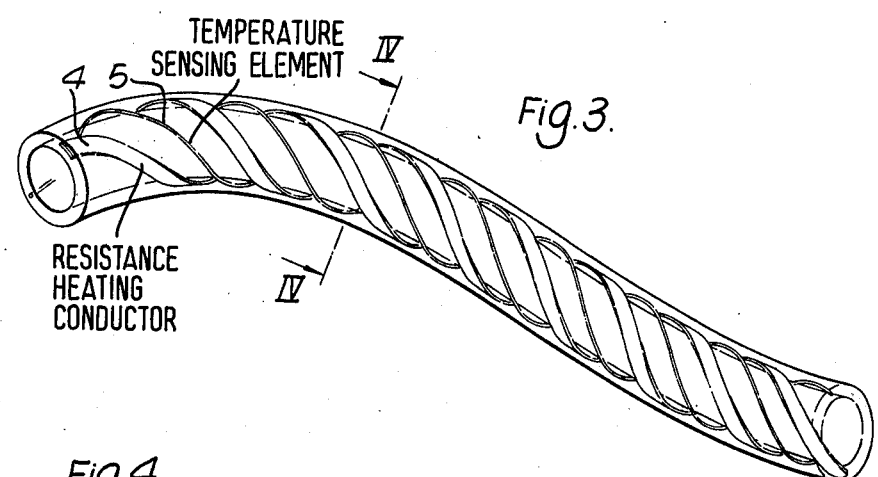
TEMPERATURE SENSING ELEMENT
Fig. 3.
RESISTANCE HEATING CONDUCTOR
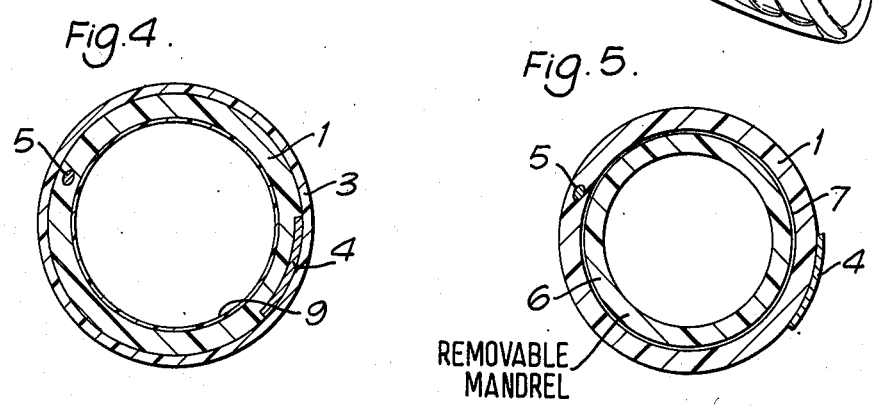
Fig. 4.
Fig. 5.
REMOVABLE MANDREL

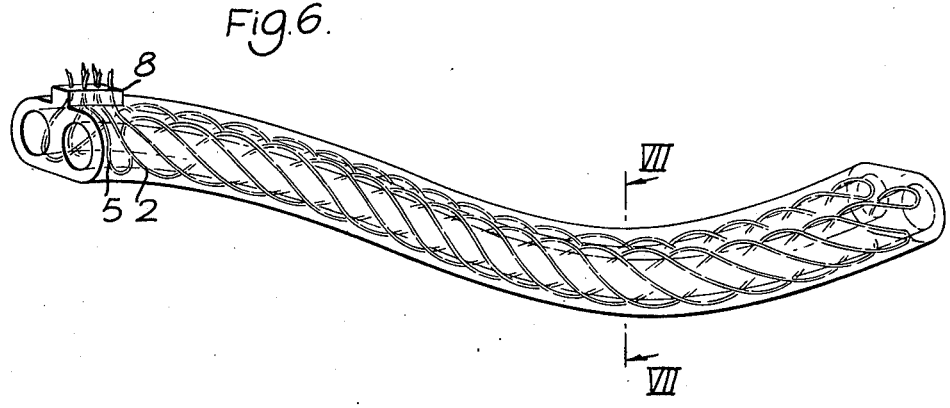
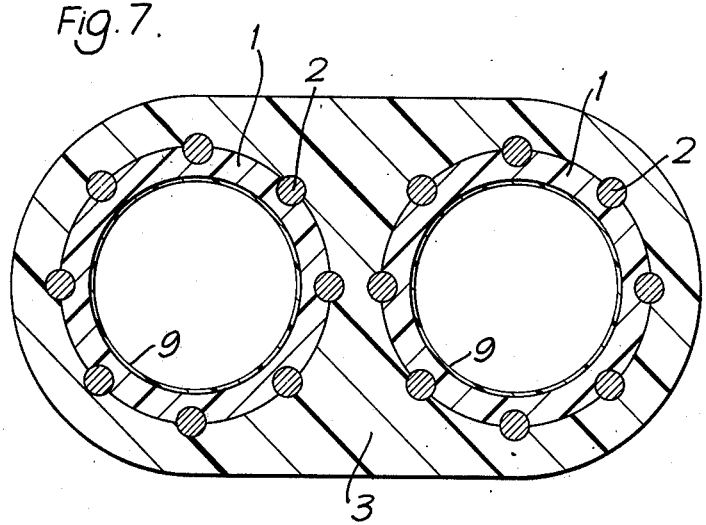

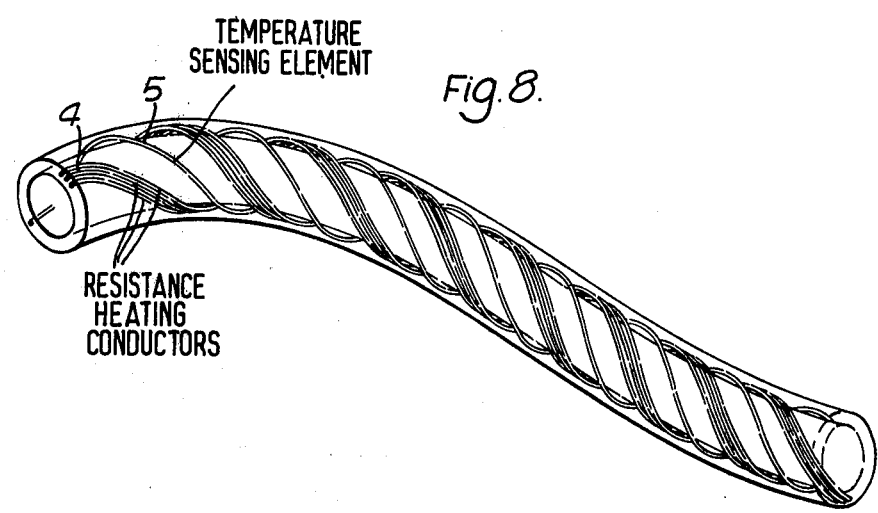

ELECTRICALLY HEATED FLEXIBLE TUBE HAVING TEMPERATURE MEASURING PROBE

The present invention relates to a flexible heating tube which is suitable especially for medical use, and to a process for its manufacture.

A heat exchanger is usually employed for keeping the temperature of a fluid constant, particularly is cases of extracorporeal circulation; this possesses the disadvantage of requiring a larger amount of fluid and of increasing the overall size of the apparatus. It is also possible to lag the tubes or to surround them with heating elements, but these devices are not easy to use around flexible tubes; furthermore, the lagging makes it impossible to follow the flow of the fluid visually in the case of a transparent tube.

According to the present invention, there is provided a flexible heating tube, especially for medical use, comprising a flexible pipe, at least one electrical resistance conductor and at least one filiform temperature measuring probe each arranged helically in the wall of said pipe.

Such a flexible heating tube is simple to manufacture and easy to employ.

The invention also provides a process for the manufacture of a flexible heating tube comprising forming a flexible pipe on a thermoplastic mandrel which does not adhere to the pipe, winding at least one electrical resistance conductor and at least one filiform temperature measuring probe in a helix on the exterior surface of the flexible pipe, forming an insulating covering on the combination thus produced, heating the tube to a temperature such that it is possible to free the mandrel by exerting a translational movement relative to the tube and withdrawing the mandrel.

In order that the invention will be better understood, the following description is given, merely by way of example, reference being made to the accompanying drawings, in which:

FIG. 1 is a perspective view of a first embodiment of transparent tube according to the invention;

FIG. 2 is an enlarged cross-section taken along the line II—II of FIG. 1.

FIG. 3 is a perspective view of a second embodiment of the tube according to the invention;

FIG. 4 is an enlarged cross-sectional view taken along the line IV—IV of FIG. 3;

FIG. 5 is a cross-sectional view through a plane perpendicular to the axis of a tube according to FIG. 3, in the course of manufacture.

FIG. 6 is a perspective view of a third embodiment;

FIG. 7 is an enlarged section on the line VII-VII of FIG. 6; and

FIG. 8 is a view similar to FIG. 1 of a still further embodiment.

The tube represented in FIGS. 1 and 2 comprises a flexible pipe 1 around which eight electrical resistance conductors 2 are arranged in a helix, and the whole is equipped externally with an insulating covering 3 firmly fixed to the flexible pipe.

The pitch of the coiling helix of the electrical conductor is advantageously between 0.2 and 20 times, and preferably between 1 and 10 times, the coil diameter of this conductor.

When using electrical conducting wires, they can be between 1 and 50, and preferably between 3 and 30 in number. The ends of the wires are connected at each end to connection terminals 8 which can be placed either at the opposite ends of the tube or at one and the same end (the electrical conductor then going to the end of the tube and back as shown in FIG. 1). In the case where the connection terminals are grouped at the same end of the tube, the current can return via a single wire of suitable resistance (for example, the wires which provide the heating effect can be made of nickel, and the current can then return via a copper wire which is a better conductor). The electrical conductors can optionally be grouped in webs brought to the same potential.

At least one of the electrical conductors can be connected to a measuring probe which is generally a temperature measuring probe. Optionally, at least one of the conductors can be used simultaneously for heating and for measuring the temperature after having been connected to a suitable device which makes it possible to provide alternately the heating effect and the switch-over to a measuring bridge.

One of the electrical conductors 5' can also be used as an earthing element.

The length and the external and internal diameters of the tube according to the invention are not critical. Advantageously, the wall thickness of the inner pipe is such that it allows the heat given off by the electrical resistance conductor to be transmitted to the fluid conveyed through the tube.

The insulating covering 3 is of such a thickness that it provides good heat insulation between the combination consisting of the conveyed fluid, the flexible pipe and the electrical conductors on the one hand and the surrounding atmosphere on the other hand.

Another embodiment of the flexible heating tube is represented in FIGS. 3 and 4. It comprises a flexible pipe 1 and an insulating covering 3 firmly fixed to this pipe. The combination of the flexible pipe and the insulating covering forms the wall of the flexible heating tube. An electrical resistance conductor 4, in the general form of a tape, and a filiform temperature measuring probe 5 are wound in a helix inside the wall of the flexible heating tube.

The electrical resistance conductor in the general form of a tape can be a shaped unit with any flattened cross-section whatsoever, and especially a rectangular cross-section, and it can also consist of a bundle of fine wires joined in webs (see FIG. 8) or braided. The characteristics of the coiling helix are of course the same as those defined above, and the helices are advantageously of the same pitch and of similar diameter and are staggered by half a pitch.

Variants lying within the ability of those skilled in the art form part of the present invention. The variants mentioned below are in no way limiting. They can optionally be combined with one another.

The outer insulating covering can consist of a heat-shrinkable sheath.

The electrical resistance conductors can be arranged in a helix inside the wall of the flexible tube when the latter is being extruded.

The electrical conductors can be enamelled or covered with materials such as polytetrafluoroethylene which provide electrical insulation, and the coiling helices can then touch one another.

The flexible pipe can be made of any flexible or semi-rigid material which may or may not be opaque, which is electrically insulating and preferably withstands rather high temperatures, and which is generally used for this type of article. Natural or synthetic rubbers, polyvinyl chloride or polyurethanes are usually employed as the material. It is, however, preferred to use elastomers such as silicone elastomers. The high heat conductivity of silicone elastomers promotes the dissipation of heat (compare MacGregor — Silicones and Their Uses — 1955 edition). It is advantageously possible to lacquer the inside of the flexible pipe by depositing a thin layer of silicone elastomer 9 at its surface in accordance with the technique described especially in the French Patent published under the Number 2,126,573.

The electrical resistance conductor can be made of any known type of electrical resistance conducting material and can, for example, consist of a metallic material or carbon.

The outer insulating covering can be made of any material similar to those used to produce the flexible pipe. It is possible optionally to lacquer it on the outside.

The flexible heating tube which is the subject of the invention can be produced, for example, in accordance with the process described below, with reference more particularly to a flexible heating tube as represented in FIGS. 3 and 4. FIG. 5 represents an intermediate stage of the process.

The flexible pipe 1 is formed, for example by extruding silicone elastomer, on a mandrel made of a heat-shrinkable material 6, the external diameter of which is substantially equal to the internal diameter desired for the heating tube. The electrical resistance conductor in the general form of a tape is wound in a helix on the non-vulcanised flexible pipe under a tension, such that the tape is in perfect contact over its entire surface with the extruded silicone elastomer forming the flexible pipe. Because of its bearing surface and because of the low mechanical tension exerted on the tape in order to maintain contact between the tape and the flexible pipe, the electrical resistance conductor remains in position on the surface of the flexible pipe whilst embedding itself slightly in the wall of the latter. Advantageously, the filiform temperature measuring probe is wound in a helix simultaneously; because of its low bearing surface and because of the mechanical tension applied, the probe becomes deeply embedded in the wall of the flexible pipe and is thus near the inner surface 7. The insulating covering 3 is formed, for example by extrusion, on the combination made up as above. The insulating covering can also be produced by the technique of immersion in a polymer solution, for example in accordance with the technique described in the examples of French Pat. No. 1,499,305.

The flexible heating tube is then heated in order to vulcanise the silicone elastomer. During the heating process, the diameter of the mandrel 6 made of a heat-shrinkable material decreases and the mandrel becomes detached from the inner surface 7 of the flexible pipe. The flexible heating tube is cut to the desired length and it is then easy to withdraw the mandrel by means of a simple translational movement. It is then possible, advantageously, to lacquer the inside and/or the outside of the flexible pipe by depositing a thin layer of silicone elastomer at its surface, in accordance with the technique described especially in the French Patent published under No. 2,126,573.

Mandrels made of materials which have a shrinkage temperature close to the vulcanisation temperature of the material forming the wall of the flexible heating tube are advantageously used as the heat-shrinkable mandrel. A mandrel made of a polyolefine, for example heat-shrinkable polyethylene, is preferably used in the case of a flexible heating tube made of silicone elastomer.

Variants of the way in which the manufacturing process is carried out, which lie within the ability of those skilled in the art, form part of the present invention. The variants mentioned below are in no way limiting.

It is possible, for example, to use a mandrel made of a thermoplastic material which is not heat-shrinkable and which does not have a sharp melting point, such that longitudinal traction exerted on this mandrel when hot makes it possible to reduce its diameter and the mandrel then detaches itself from the inner surface of the heating tube and can be withdrawn easily. Polymers such as polyolefines or halogenated vinyl polymers, or mixture of polymers can be used to produce this mandrel; in the case of a heating tube made of silicone elastomer, it will be preferred to use a mandrel made of polyvinyl chloride.

The electrical resistance conductor can be a round wire, like the temperature measuring probe, both embedding themselves in the wall of the flexible pipe. Because it has a larger diameter and because of its lower tension during the winding process, the electrical resistance conductor becomes only slightly embedded in the wall of the flexible pipe.

The process which is the subject of the invention is in no way limited to the manufacture of a flexible heating tube comprising only one electrical conductor and only one temperature measuring probe, but covers the manufacture of heating tubes comprising several electrical conductors and several temperature measuring probes.

The process which is the subject of the invention can optionally be carried out by using a mandrel, the length of which is limited to the length desired for the flexible heating tube.

As shown in FIGS. 6 and 7, it is possible to group at least two flexible heating tubes 1 inside a single insulating covering 3, it being possible for the flexible tubes optionally to be of different diameters. To do this, after having extruded two flexible pipes 1 and after having formed the coils 2 of electrical resistance conductors and temperture measuring probes on the latter in accordance with the technique described above, the tubes are placed side by side and the insulating covering 3 is extruded on the combination thus formed. The insulating covering can advantageously consist of an elastomer with a cellular structure. It is also possible to mould an insulating covering from a cold-curable organopolysiloxane elastomer. The insulating covering can also consist of a heat-shrinkable material. The heating resistances of such flexible heating tubes are preferably connected in series; this has the advantage of positioning the electrical connection at the same end of the tube. The heating tubes with a double flexible pipe are particularly valuable in the medical field for circuits for extracorporeal circulation; in effect, by making it possible both for the blood to flow out and to return, they reduce both the number of tubes and the number of electrical conductor connections necessary.

It is thus possible to produce great lengths of such tubes and to do so in all the diameters usually employed. These tubes can be cut to the required length, the electrical conductors being sheared by the usual means. It is then easy to free the ends of the electrical conductors and to connect them to a source of electric current, generally at a very low voltage. Of course, it is advantageous to equip these tubes with nozzles and/or suitable connections of any known types. The flexible heating tube is connected in a leakproof manner in accordance with the usual techniques to an apparatus which can accept such tubes. The ends of the electrical conductors are connected to a suitable source of current. It is thus possible to connect — hydraulically and/or electrically — several of these tubes in series and/or in parallel. A fluid — a liquid or a gas — can flow inside each flexible tube. When an electric current is passed through the electrical resistance conductors 2, heat is given off by the Joule effect. This heat is transmitted through the wall of the inner flexible pipe to the fluid contained inside.

The flexible heating tube which is the subject of the invention possesses numerous advantages.

The materials used for manufacturing the flexible heating tube provide it with complete leakproofness to fluids, which is necessary for conveying biological fluids. The materials used are moreover compatible with biological fluids and the lacquer finish of the inner pipe is particularly advantageous for conveying blood. The flexible heating tubes can be sterilised by radiation, and the tubes made of silicone elastomer are advantageously sterilised by means of dry heat.

It is preferable for the tube to be transparent in order to make it possible visually to follow the flow of the biological liquids conveyed.

The flexible heating tube which is the subject of the invention makes it possible to keep a fluid at a particular temperature above ambient temperature. The uniform distribution of the electrical conductors makes it possible to transmit a moderate amount of heat which is well distributed throughout a section and over the entire length of the heating tube, avoiding local overheating effects. By connecting the electrical conductors of the heating tube to a suitable control device it is possible to keep the temperature of the conveyed fluid constant despite variations in flow rate.

The process for manufacturing the flexible heating tube possesses numerous advantages.

Thus this process is easy to carry out because, due to the fact that the electrical conductors become embedded, their relative positions are fixed and sideways movements, for example due to slipping, are not possible.

Another great advantage connected with the use of this process is that the information relating to temperature provided by the measuring probe is more representative of the temperature of the fluid conveyed; in fact, the measuring probe is placed as close as possible to the inner surface of the flexible heating tube, that is to say as close as possible to the fluid, the temperature of which it is desired to control.

The manufacturing process which is the subject of the present invention possesses the advantage of requiring only a flexible pipe of low thickness in order to be able to produce the helical coils of the electrical resistance conductor and of the temperature probe, the flexible pipe being held by the heat-shrinkable mandrel during the winding operation. It is consequently easier to transmit heat from the electrical resistance conductor to the fluid conveyed. At the same time, in order to provide the heating tube with sufficient rigidity, the thickness of the outer insulating covering can be greater, and consequently heat losses to the surrounding atmosphere can be reduced.

The manufacturing process also possesses the advantage of requiring only one vulcanisation operation.

The use of a flexible heating tube according to the invention is particularly valuable in extracorporeal blood circulation because it makes it possible to dispense with heat exchangers, avoiding heat losses in the lines for conveying the blood between the patient and the extracorporeal circulation apparatus. It also makes it possible to reheat the blood after an operation carried out under conditions of hypothermia. Its use in the artificial lung apparatus makes it possible to prevent condensation when conveying moist air. The tube according to the invention can also find numerous laboratory applications.

The characteristics and the capabilities of such a heating tube are illustrated by the following example:

EXAMPLE

A flexible heating tube made of silicone elastomer, of length 2.5 m, is manufactured. The flexible pipe having an internal diameter of 10 mm and a wall thickness of 1.3 mm, and has wound around the latter in a helix 24 electrical resistance conductors (12 on the outward and 12 on the return path) made of nickel of diameter 0.20 mm, the pitch of the helin being 72 mm. The electrical conductors are distributed uniformly over the wall of the flexible pipe in a cross-section of the tube. The outer insulating covering consists of a 1.5 mm layer of silicone elastomer.

The tube according to the above embodiment is placed at ambient temperature, and the lowering of the temperature of water ($\Delta$ T) between the inlet and the outlet of the tube when no current is passed through the electrical conductors was measured for various water flow rates. The power which it suffices to apply in order to keep the temperature of the water constant while passing from one end to the other of the tube was measured.

The table below gives the results of the experiments for water flow rates of 1, 2, 3 and 4 $l$/minute, the electrical conductors being supplied with direct current from a 12 volt battery during the heating process.

| F l/minute | $T_A$ °C | $T_I$ °C | $T_O$ °C | $\Delta T$ °C | Power required to compensate for $\Delta T$ | | |
|---|---|---|---|---|---|---|---|
| | | | | | V | I | W |
| 1 | 23.6 | 39.2 | 38.92 | 0.28 | 7.6 | 7 | 53 |
| 2 | 23.8 | 39.2 | 39.01 | 0.19 | 8.8 | 8 | 70.4 |
| 3 | 23.8 | 39 | 38.83 | 0.17 | 9 | 10 | 90 |

-continued

| F 1/minute | $T_A$ °C | $T_I$ °C | $T_O$ °C | ΔT °C | Power required to compensate for ΔT | | |
|---|---|---|---|---|---|---|---|
| | | | | | V | I | W |
| 4 | 24 | 39 | 38.855 | 0.145 | 9.9 | 10.8 | 107 |

F : Flow rate of water through the tube in 1/minute
$T_A$: Ambient temperature, in ° C
$T_I$: Temperature of the water at the inlet of the tube, in ° C
$T_O$: Temperature of the water at the outlet of the tube, in ° C, with no current passing through the electrical conductors
ΔT : Lowering of the temperature of the water between the inlet and the outlet of the tube ($T_I - T_O = $ ΔT)
W : Power dissipated in the electrical conductors, sufficient to compensate ΔT, in watts.
V : Voltage applied to the electrical conductors, in volts
I : Current passing through the electrical conductors, in amperes.

I claim:

1. A flexible heating tube, especially for medical use, comprising a flexible pipe of transparent plastics material, at least one electrical helical resistance heating conductor and at least one helical filiform temperature measuring resistance probe being wound on the same axis and being embedded in the wall of the said pipe, and in surrounding relation to the bore in the pipe, the helical turns of the at least one electrical resistance conductor and of the at least one temperature measuring probe being of the same pitch, and being coextensive along the length of the pipe and electrical connection terminals at at least one end of said pipe connected to said at least one heating conductor and said at least one temperature measuring probe.

2. A flexible heating tube as claimed in claim 1, wherein the flexible pipe includes an inner pipe around which said at least one electrical resistance heating conductor and at least one temperature measuring probe are helically arranged and an outer insulating covering is firmly fixed to said inner pipe.

3. A flexible heating tube as claimed in claim 2, wherein the insulating covering consists of a heat-shrinkable sheet.

4. A flexible heating tube as claimed in claim 2, wherein the inner flexible pipe and the insulating covering are made of silicone elastomer.

5. A flexible heating tube as claimed in claim 1, wherein the electrical turns of the at least one electrical resistance heating conductor and of the at least one temperature measuring probe are substantially of the same diameter, and are staggered by half a pitch.

6. A flexible heating tube as claimed in claim 1, wherein the pitch of the coils of the helices is between 0.2 and 20 times the coil diameter of said at least one electrical resistance leading conductor.

7. A flexible heating tube as claimed in claim 1, wherein a plurality of electrical resistance heating conductors are provided and are grouped in webs adapted to be connected to one and the same source of potential.

8. A flexible heating tube as claimed in claim 1, wherein a plurality of said electrical resistance heating conductors are provided.

9. A flexible heating tube as claimed in claim 1 wherein there are a plurality of said resistance heating conductors, at least one of said conductors being connected separately whereby it may be used as an earthing element.

10. A flexible heating tube as claimed in claim 1, wherein the at least one electrical resistance heating conductor comprises a metal tape.

11. A flexible heating tube as claimed in claim 1, and further comprising lacquering on at least one of the inside and outside surfaces of the pipe.

12. A flexible heating tube, especially for medical use, comrising two flexible pipes of transparent plastics material, at least one helical electrical resistance heating conductor and at least one helical filiform temperature measuring resistance probe being wound on the same axis and being embedded in the wall of each of said pipes and in surrounding relation to the bore in the pipe, the helical turns of the at least one electrical resistance conductor and of the at least one temperature measuring probe of each pipe being of the same pitch, the electrical resistance conductor and the temperature measuring probe of each pipe being coextensive along the length of the pipe, at least one electrical connection terminal at at least one end of said tube connected to said at least one heating conductor and said at least one temperature measuring probe and an outer insulating covering extending over both of said pipes simultaneously.

* * * * *